United States Patent [19]

Bucalo

[11] 3,998,211
[45] Dec. 21, 1976

[54] STRUCTURES FOR GROWING CULTURES WITHIN HUMAN AND ANIMAL BODIES

[76] Inventor: Louis Bucalo, 155 Roberts St., Holbrook, N.Y. 11741

[22] Filed: Dec. 20, 1974

[21] Appl. No.: 534,893

Related U.S. Application Data

[60] Continuation-in-part of Ser. No. 499,925, Aug. 23, 1974, Pat. No. 3,934,575, and Ser. No. 499,926, Aug. 23, 1974, Pat. No. 3,924,607, each is a division of Ser. No. 329,862, Feb. 5, 1973, Pat. No. 3,842,166.

[52] U.S. Cl. .............................. 128/2 F; 128/2 W; 128/275; 195/139
[51] Int. Cl.² ......................................... A61B 10/00
[58] Field of Search .......... 128/1 R, 2 W, 2 R, 2 F, 128/260, 275; 195/103.5 R, 139, 140

[56] References Cited
UNITED STATES PATENTS

| | | | |
|---|---|---|---|
| 2,905,169 | 9/1959 | Nieburgs | 128/2 B |
| 3,308,039 | 3/1967 | Nelson | 195/140 |
| 3,368,549 | 2/1968 | Barr et al. | 128/2 W |
| 3,450,129 | 6/1969 | Avery et al. | 128/2 W |
| 3,579,303 | 5/1971 | Pickering | 195/139 X |
| 3,688,763 | 9/1972 | Cromarty | 128/2 F X |
| 3,844,285 | 10/1974 | Laby | 128/260 |
| 3,853,116 | 12/1974 | Bucalo | 128/1 R |

*Primary Examiner*—Kyle L. Howell
*Attorney, Agent, or Firm*—Steinberg and Blake

[57] ABSTRACT

Structures for enabling certain microorganisms, if they are present, to grow in nutrients while the latter are situated within a human or animal body. The nutrient for the microorganism is situated within an enclosure which is introduced into a cavity of the body with the enclosure preventing any communication between fluids within the enclosure and the body which surrounds the enclosure, so that cultures grown from microorganisms in the nutrient will not influence the body. When the enclosure is situated within the body cavity, conditions are created for transferring one or more microorganisms from the exterior of the enclosure to the interior thereof into contact with the nutrient, these conditions for transfer of the microorganism being created by way of a transfer structure connected with the enclosure and capable of transferring a microorganism to the nutrient within the enclosure while the latter remains closed at least to an extent sufficient to prevent any fluids from escaping from the enclosure to the exterior thereof.

14 Claims, 7 Drawing Figures

U.S. Patent Dec. 21, 1976 Sheet 1 of 2 3,998,211
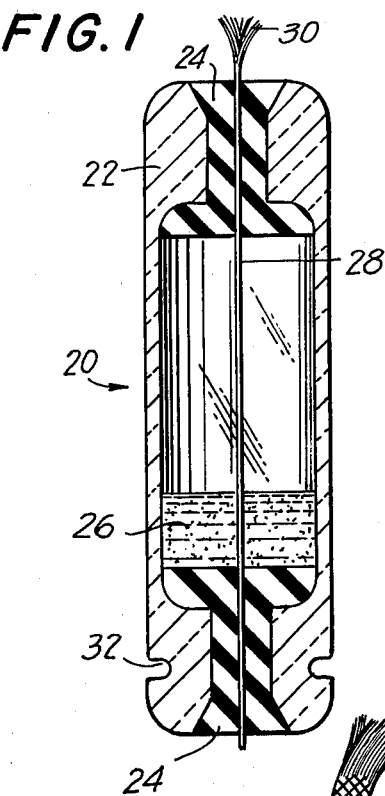
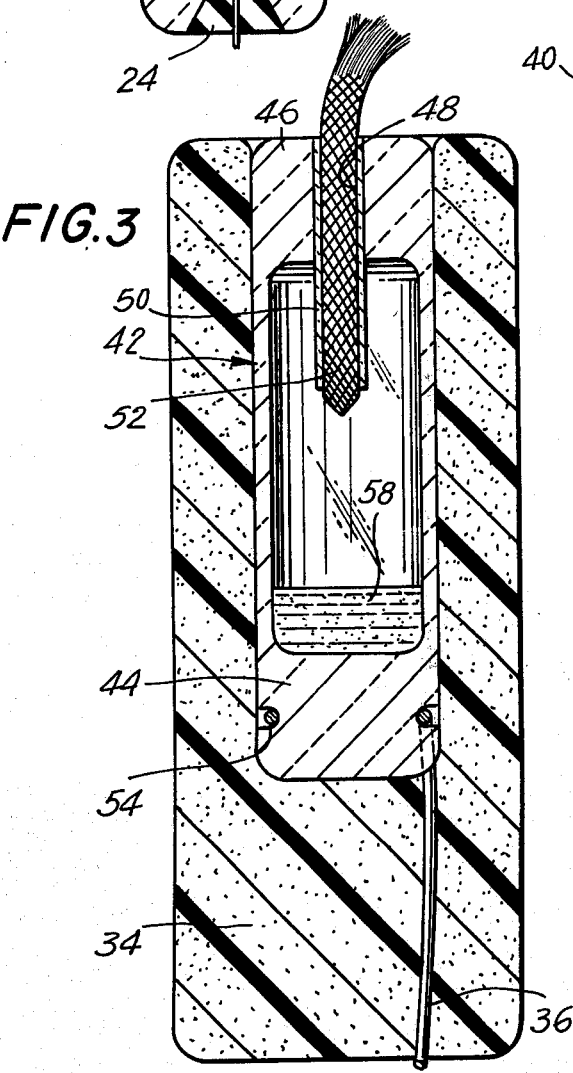
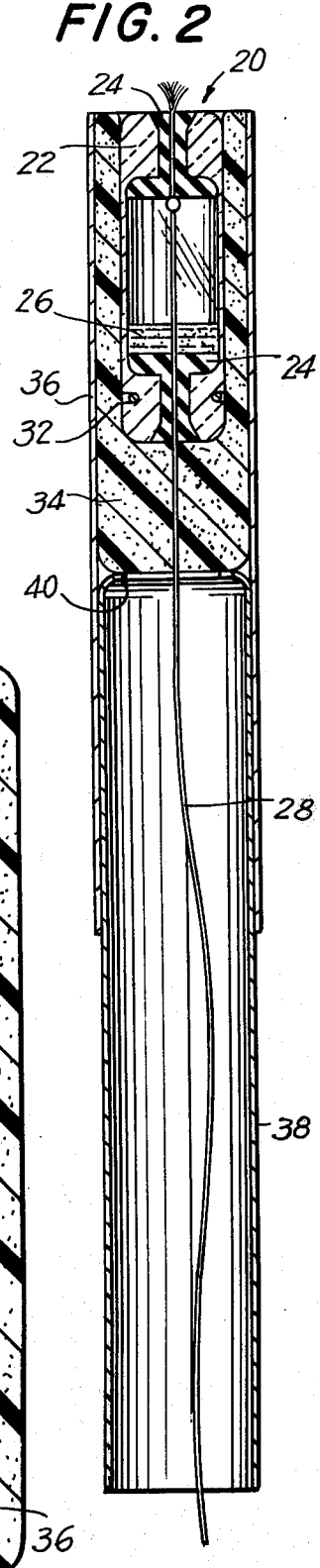
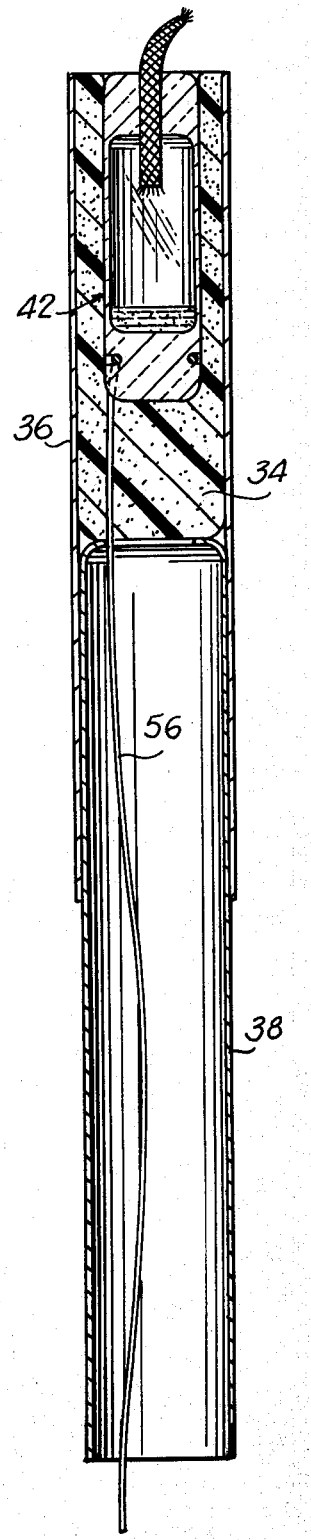

STRUCTURES FOR GROWING CULTURES WITHIN HUMAN AND ANIMAL BODIES

CROSS REFERENCE TO RELATED APPLICATIONS

The present application is a continuation-in-part of copending applications Ser. Nos. 499,925, now U.S. Pat. No. 3,934,575 and 499,926, now Pat. No. 3,924,607 both filed Aug. 23, 1974, the latter applications both being divisions of application Ser. No. 329,862, filed Feb. 5, 1973, now U.S. Pat. No. 3,842,166.

BACKGROUND OF THE INVENTION

The present invention relates to culturing devices.

Thus, the present invention relates to devices for growing cultures from microorganisms so that by inspection of the cultures it is possible to determine the presence of certain microorganisms.

At the present time when the presence of a given microorganism is suspected at a given part of the body of an individual, in order to determine whether or not in fact such a microorganism is present, it is conventional to transfer a body fluid which is suspected of carrying the microorganism to a suitable growth medium where the microorganism, if in fact it is present, will grow so that by inspection of the growth medium the presence or absence of the microorganism can be determined. For such purposes it is conventional to apply a swab to a part of the body where the presence of a given microorganism is suspected, this swab removing part of the body fluid such as mucous or the like which is suspected of carrying the microoganism, and then the swab is placed in contact with a suitable nutrient for transferring the body fluid with the suspected microorganism therein to the nutrient medium. Thereafter the nutrient is placed for example, in a suitable incubator for a given period of time in an atmosphere which is favorable for growth of the microorganism, and after elapse of this period of time, the growth medium is inspected to determine whether or not in fact the suspected microorgansims have grown and are therefore present in the body.

Procedures and devices of the above type have inherent disadvantages. Thus, there is a considerable inconvenience in requiring a physician or other skilled individual to extract from the body of an individual materials which are suspected of containing a given microorganism and then transferring the extracted material to a growth medium which must then be placed in an atmosphere suitable for growth. In addition to the inconvenience of these procedures, a considerable amount of equipment is required, and very often physicians will mail swabs with specimens thereon to laboratories for testing. Thus, under these latter conditions a considerable delay is involved as well as a considerable risk that the microorganisms, if they are present, will die during the interval between removal from the body and contact with a nutrient at a laboratory, for example, after transportation time has elapsed.

Also, certain microorganisms cannot remain alive when subjected even to a slight temperature change upon leaving the body.

Moreover, completely aside from the above factors, the conditions under which microorganisms are artificially grown cannot fail to be different from the conditions which obtain in the body where the microorganism may be located. Because of these different growing conditions, it is possible to arrive at inaccurate results according to which unnecessary treatments will be given to an individual or according to which necessary treatments will not be given.

SUMMARY OF THE INVENTION

It is accordingly a primary object of the present invention to provide structures which will avoid the above drawbacks.

Thus, it is an object of the present invention to provide structures according to which it is possible to obtain cultures of given microorganisms by growing the cultures directly within the body where the presence of the microorganisms is suspected, so that in this way all of the inconveniences with respect to transfer of the microorganism to the exterior of the body to a suitable growth medium which must be placed in a special atmosphere are avoided, while at the same time any delay occasioned by delivering the suspected microorganism to a laboratory or the like is also avoided.

It is furthermore an object of the present invention to provide structures of the above type which will create no particular discomfort and which will in no way result in deterioration of the health condition of a given individual or animal.

It is furthermore an object of the present invention to provide structures of the above type according to which exceedingly simple and convenient manipulations are all that are required in connection with growth of cultures within the body.

Furthermore, it is an object of the present invention to provide culture-growing structures which are relatively simple and inexpensive while at the same time being fully hygienic.

In addition it is an object of the present invention to provide structures of the above type which lend themselves to determination of the presence of a large variety of microorganisms in a manner which will give a clear indication of the presence or absence of the microorganisms.

According to the invention an enclosure, which has a suitable nutrient in its interior, is introduced into a body cavity in such a way that a part of the enclosure is located in the immediate vicinity of a location where it is suspected that certain microorganisms are present while the nutrient is normally situated beneath this part of the enclosure. With the enclosure thus situated in the body cavity, conditions are created for transferring a microorganism from the location where the presence thereof is suspected into the interior of the enclosure into contact with the nutrient therein. After the enclosure remains in the body for a time sufficient for growth of a culture in the nutrient from the suspected microorganism, the enclosure is removed and then the nutrient may be checked for determination of the presence or absence of the suspected microorganism.

The structure of the invention includes an enclosure means which has a suitable nutrient means in its interior and which is provided with means to prevent fluid from flowing from the interior to the exterior of the enclosure means. The enclosure means of the invention is designed to be accommodated in a body cavity in such a way that one part of the enclosure means is at an elevation higher than another part thereof where the nutrient means is located with this one part of the enclosure means being adapted to be situated in the immediate vicinity of a location where the presence of certain microorganisms is suspected. At this one part of the enclosure means is a transfer means of the invention capable of bringing about the transfer of a microorganism from the exterior of the enclosure means at the region of this one part thereof to the interior thereof into contact with the nutrient means therein.

BRIEF DESCRIPTION OF THE DRAWINGS

The invention is illustrated by way of example in the accompanying drawings which form part of this application and in which:

FIG. 1 is a sectional elevation of one embodiment of a structure of the invention;

FIG. 2 is a longitudinal sectional elevation of a structure for supporting the device of FIG. 1 and for introducing the same into a body cavity;

FIG. 3 is a sectional elevation of another embodiment of a device of the invention;

FIG. 4 is a sectional elevation showing structures similar to that of FIG. 2 for introducing the device of FIG. 3 into a body cavity;

FIG. 8 shows a variation which is adapted to have a predetermined gaseous atmosphere generated.

DESCRIPTION OF PREFERRED EMBODIMENTS

Figure 5:
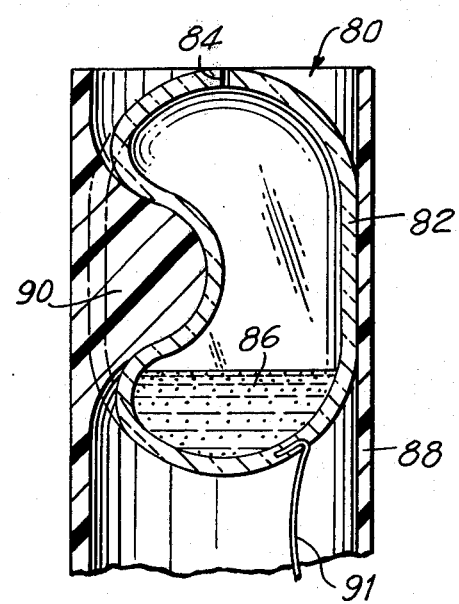
FIGS. 5–7 are respectively schematic sectional elevations of various possible embodiments of the invention with means for initially holding the enclosures in a compressed condition of restricted interior volume.

Referring first to FIG. 1, there is illustrated therein an enclosure means 20 in the form of an elongated container 22 made of a suitable clear, transparent plastic such as polyethylene which may be relatively soft so that it has a certain amount of flexibility, although this latter property is not essential with the embodiment of FIG. 1. The opposed ends of the elongated enclosure means 20 are provided with a pair of opposed closure plug means 24 which close openings formed in the plastic container 22, in the manner illustrated in FIG. 1. These plugs 24 may be made of a material such as rubber or any other suitable plastic. Thus it will be seen that the enclosure means 20 is completely closed. However, before this enclosure means 20 is completely closed a nutrient means 26 is situated therein. This nutrient means 26 may be in the form of a suitable broth which can be in its entirety in the form of a liquid although it can also be absorbed in a suitable medium such as cotton fibers and can have any desired viscosity. The composition of the nutrient means 26 is well known in connection with growth of cultures, this nutrient means 26 being capable of growing a culture from microorganisms which are placed in contact with the nutrient means 26.

In accordance with the method of the invention the enclosure means 20 is introduced into a body cavity in such a way that the upper part of the enclosure, as viewed in FIG. 1, is situated in close proximity to a location where it is suspected that certain microorganisms are present. With the method of the invention after this enclosure and nutrient therein are situated in the above manner in the body cavity, conditions are created for transferring a microorganism from the location where the presence thereof is suspected into the interior of the enclosure means into engagement with the nutrient means therein. These conditions are created in the embodiment of FIG. 1 by way of an elongated filament or string 28 which passes completely through the plugs 24 while frictionally engaging the same. Thus it will be seen that while the filament or string 28 passes through the closure plugs 24 nevertheless the interior of the enclosure 22 remains closed. At the upper part of the enclosure 20 which is situated in the vicinity of the suspected microorganism, the string 28 carries a means 30 for receiving a microorganism if indeed it is present at the location where the upper end of the enclosure of FIG. 1 is situated. This means can take the form of a suitable wick or other absorbent medium connected to the outer end of the filament 28 which is shown at the top of FIG. 1. For this purpose it is only necessary to abraid the filament 28 so as to fray the outer end portion thereof situated above the enclosure means 20, as viewed in FIG. 1, and in this way a part of the filament itself forms the means 30 for receiving the microorganism if it is present. Thus this means 30 will engage mucous or the like which may contain the suspected microorganism, so that in this way the microorganism is received by the means 30.

With this structure of the invention which is shown in FIG. 1, after it is situated in the selected location, according to the method of the invention, the monofilament 28 is pulled downwardly as viewed in FIG. 1, so that the receiving means 30 with the microorganism received thereby is pulled through the upper closure plug 24 into the interior of the container 22. Once this means 30 moves through the upper plug 24 it will simply fall to the nutrient means 26 to place any microorganism in the means 30 in contact with the nutrient means. The operator can feel the reduction in the force required to pull the string 28 as soon as the means 30 moves into the interior of the enclosure beyond the upper closure plug 24, so that the operator will then know that no further pulling of the string 28 is required. If desired, however, the string 28 can be pulled completely through the lower plug 24 also so that the operator can completely remove the string 28 if so desired.

It is to be noted that the container 22 is provided at the region of its lower end with an exterior groove 32 capable of receiving one end region of a string which can be fastened at the groove 32 to the enclosure 22 so that through such a string it is possible in any event to remove the enclosure from the body cavity.

This structure is permitted to remain in the body cavity for a length of time sufficient for the culture to grow, and thereafter it is removed and the culture medium can be inspected directly through the clear plastic material to determine the presence of certain microorganisms. Also, through one or both of the plugs 24 the nutrient means 26 is accessible for application of suitable staining mediums, for example, which can aid in recognizing certain microorganisms.

Referring now to FIG. 2, it will be seen that the entire device 20 of FIG. 1 is situated within a cup-shaped body 34 made of a soft material such as a suitable foam polyethylene, for example. Both the cup-shaped body 34 as well as the container 22 are of a circular cross section, and the cup-shaped body 34 has a top open end, as viewed in FIG. 2, where the top end of the container 22 is exposed so that the portion 30 of the filament 28 will also be exposed. The cup-shaped body 34 is introduced into the body cavity with the device 22 seated in the cup-shaped body in the manner illustrated in FIG. 2, so that by way of the soft cup-shaped body 34 there will be no discomfort to the individual.

In order to be able conveniently to introduce the device of the invention into a body cavity, the cup-shaped body 34 is situated in the interior of an elongated outer tube 36 made of any suitable relatively rigid cardboard, plastic, or the like. Telescoped within the outer tube 36 is a pusher 38 which may be in the form of a tube having at its upper end, as viewed in FIG. 2, an inwardly directed flange 40 which will engage the bottom end of the body 34 in the manner illustrated in FIG. 2.

Thus, with this construction it is possible very conveniently to introduce the structure of the invention into a body cavity. For example if the portion 30 of the filament 28 is to be situated in engagement with the cervix, then the telescoped elements 36 and 38 are operated in the manner of conventional elements of this type used to introduce a cylindrical type of tampon into the vagina during the menstrual period. Thus, the upper end of the tube 36, as viewed in FIG. 2, will be initially introduced into the vagina, and then the pusher 38 will be advanced to displace the cup-shaped body 34 out of the tube 36 and along the interior of the vagina until a resistance is felt indicating that the upper end of the container 22 and the part 30 of the filament 28 are situated next to the cervix. With the cup-shaped body 34 thus held in this way at the desired location, the operator will pull on the string 28 which it will be noted extends completely through and beyond the tube 38. Thus, any body fluid such as mucosa or the like situated at the cervix and carrying possible microorganisms such as those of ghonorrea, for example, or any vaginitis microorganisms, will become situated in the portion 30 together with mucosa or the like absorbed thereby, and such microorganisms if they are present will be pulled together with the string 28 through the upper plug portion 24 while the container remains closed. The pulling of the string in the above manner is delayed, however, until the container has been in the body for a time sufficient for the entire assembly to assume the temperature of the body. As was indicated above once the portion 30 of the string 28 moves inwardly beyond the plug 24 shown at the top end of the container 22 in FIG. 1, the operator will feel reduction in the resistance to pulling on the filament 28, and thus it will be known that the portion 30 has reached the interior of the container 22 and can fall freely into engagement with the nutrient 26. If desired, however, the operator can continue to pull on the string 28 so as to remove the latter completely through the lower plug 24 also. It will be noted that in the embodiment shown in FIG. 2, the string 28 has in the interior of the enclosure an enlargement which will limit pulling of the string out of the enclosure. In any case, once the part 30 has engaged the nutrient 26 the tube 38 can be removed while the cup-shaped body 34 together with the device 20 remains in the body so that microorganisms, if they are present, can grow in the nutrient means 26 while the latter together with the container 22 remains in the body.

After a given length of time it is possible to remove the body 34 together with the device 20 from the body cavity. For this purpose a suitable string may be attached to the groove 32 or if the string 28 remains it can be used or this purpose.

It is to be noted that with the above-described structure of the present invention it is possible to grow cultures from suspected microorganisms directly in the body cavity where the presence of the microorganisms is suspected so as to closely simulate for the growth of the culture the conditions which are present in the body cavity itself. In addition, because the container 22 is completely closed there is minimum possibility of providing in the body itself conditions which will enhance the growth of the microorganisms in a manner which will cause greater deterioration to the body itself from the growth of the microorgansims. Thus with the method and structure of the invention the body is safely shielded from any possible ill effects resulting from growing the microorganisms in the body itself.

As was indicated above, once the cup 34 is removed it is a simple matter to remove the device 22 and then carry out whatever steps are required to determine whether or not a culture growth in the nutrient 26 contains the suspected microorganisms.

A further variation of the structure of the invention is shown in FIG. 3.

According to this embodiment the device 42 is in the form of container similar to the container 22 made of the same material. However in this case the device 42 has a closed bottom end 44, as viewed in FIG. 3, while the upper end 46 is formed with an elongated opening 48 which is of relatively small diameter. This opening 48 is lined with an elongated plastic or glass tube 50 which has compressed in its interior a wick 52, as illustrated in FIG. 3. This wick 52 has an upper free end portion which projects beyond the upper end of the container 42 in the manner shown in FIG. 3. Moreover the entire container is seated in a cup-shaped body 34 which is identical with that of FIG. 2. However it will be noted that in FIG. 3 the groove 54 which corresponds to the groove 32 of FIG. 1 has a string 56 situated therein and extending through and beyond the soft cup-shaped body 34 in the manner illustrated.

This structure which is shown in FIG. 3 is seated in an outer tube 36 in the manner shown in FIG. 4 with a pusher 38 being provided as was the case with FIG. 2. Thus the embodiment of FIG. 3 can be introduced into a body cavity in the same way the embodiment of FIG. 1. In this case, however, the cup-shaped body 34 together with the device 42 is simply placed in the body cavity with the upper free end of the wick at the upper part of the container 42 being situated at the region where the presence of certain microorganisms is suspected. After the length of time required for growth of a suitable culture the entire device 42 together with the body 34 are removed by pulling on the string 56.

It is to be noted that the embodiment of FIG. 3 will operate in a particular manner. Thus, the wick 52 by being compressed within the tube 50 which in turn has a sealed engagement as its outer surface in the opening of the part 46 of container 42 serves to substantially close the container while at the same time permitting by the absorbent action of the wick a body fluid with suspected microorganisms therein to pass through the wick into the interior of the container 42 where the nutrient 58 is situated. This body fluid with suspected microorganisms therein will form at the lower interior end of the wick, as viewed in FIG. 3, a drop which will separate itself from and fall from the wick to the nutrient medium 58. As successive droplets of body fluid with suspected microorganisms therein fall from the wick the level of the nutrient medium, which may be a liquid broth, for example, will arise toward the wick thus reducing the interior space above the liquid material in the interior of the container 42. In this way the pressure of the latter space will increase to limit the extent to which the dripping of the body fluid into the interior of the container 42 can take place. The plastic or glass tube 50 prevents any liquid which may be situated in the interior of the container beside the wick from engaging the latter. At the same time, because of the increased pressure in the space above the liquid in the container 42 the dripping will stop because an equilibrium will be reached when the presssure becomes great enough to prevent any further fluid from entering through the wick, and thus in this case also there is provided a container capable of growing a culture in its interior without in any way contaminating the body in which the device of the invention is situated.

As was the case with FIG. 1, the device of FIG. 3 is removed after a given time and then suitable procedures can be carried out with respect to the nutrient to determine whether or not any culture which grows therein contains suspected microorganisms.

Referring now to FIG. 5, the embodiment of the invention illustrated therein also includes a device 80 having a flexible resilient container 82 made of a clear plastic. However, in the case of FIG. 5 the container 80 is only provided at its upper end, which becomes situated uppermost when introduced into the body, with a slit or with a minute pinhole type of opening 84. A nutrient means 86, corresponding to any of the nutrient means referred to above, is situated in the container 82 as illustrated.

According to this embodiment there is also an outer tube 88 through which the device 80 is pushed into the interior of the body cavity in the manner described above in connection with FIGS. 2 and 4. However, in this case the outer tube 88 is provided at its interior with a bulging portion 90 which serves to deform the container 82 in the manner illustrated in FIG. 5, so that in this way the container 82 has a restricted interior volume. The pusher which is used with the outer tube 80 differs from the pusher of FIGS. 2 and 4 in that this particular pusher will have a portion which is cut away so as to clear the bulging portion 90 while the pusher displaces the container 82 past the bulging portion 90. The result is that the container 82 is introduced into the body cavity in a compressed condition of restricted interior volume. As soon as the unit 82, however, moves beyond the bulging portion 90, it will expand slowly due to its inherent resiliency, drawing fluid in through the minute opening 84, and if any of this fluid has the suspected microorganisms they will of course contact the nutrient means 86. In this case also the container 82 has a suitable string attached thereto as, for example, a string 91 embedded in a wall of the container 82 and projecting from this wall so as to be accessible for withdrawing the container 82 after a given length of time sufficient for microorganisms to grow in the nutrient means 86 while the container 82 remains in the body cavity.

Of course, with this embodiment of FIG. 5 it is also possible to situate the container 82 in a cup-shaped body made of a soft material, as was the case with the embodiments of FIGS. 1–3, and in this event the bulging portion 90 would compress the soft cup-shaped body and act through the latter on the container 82 in order to compress the latter in the manner shown in FIG. 5. Thus with this simple embodiment of FIG. 5 it is also possible to achieve an automatic expansion of the container 82 when its slit 84 becomes situated at the location where it is suspected that certain microorganisms are present, so that if indeed these microorganisms are present they will be sucked in through the slit 84 into the interior of the container 82 together with any body fluids which carry the microorganisms.

Figure 6:
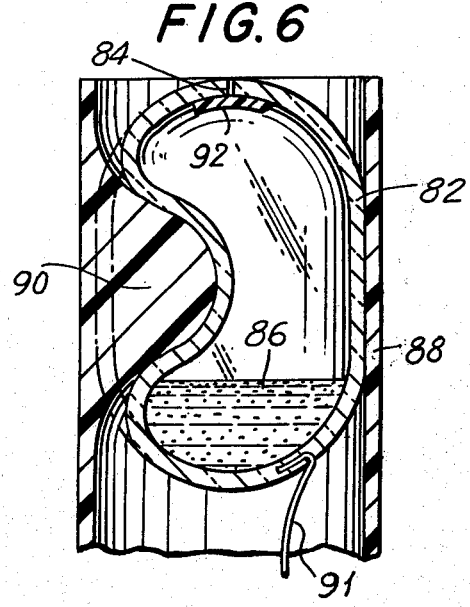

The embodiment of FIG. 6 is identical with that of FIG. 5, except for the fact that with the embodiment of FIG. 6 the container 82 is provided in its interior with a flap valve 92 which normally maintains the small minute opening 84 closed but which of course is capable of turning inwardly away from the opening 84, the flap valve 92 being fixed, for example, to the inner surface of the container 82 only at the right edge region of the flap valve 92, as viewed in FIG. 6. Thus, with this embodiment, all of the features described above in connection with FIG. 5 will be the same, the only difference being that the flap valve 92 automatically yields to permit fluid, with suspected microorganisms therein, to enter into the container 82, while the flap valve 92 will reliably prevent any fluid from escaping from the interior of the container 82. Thus with the embodiment of FIG. 6 it is possible to provide an opening 84 which is somewhat larger than the slit 84 of the embodiment of FIG. 5.

Figure 7:
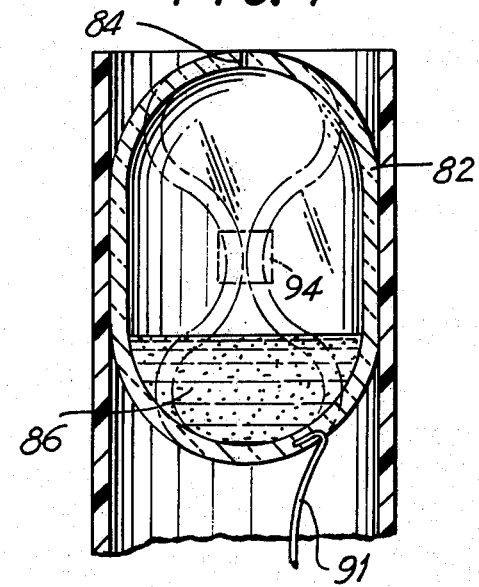

With the embodiment of the invention which is illustrated in FIG. 7, there is also a container 82 which is identical with the container 82 of FIG. 5. However, in this case, the container 82 is initially maintained in a compressed condition of restricted interior volume, as shown in dotted lines in FIG. 7, by way of a ring 94 which is made of a material which will dissolve in the interior of the body. Such materials are well known. Thus, with this embodiment before the container is introduced it is compressed to the dotted line condition and maintained in this compressed condition by the ring 94, and then the container 82 of FIG. 7 is introduced into the interior of the body cavity in the manner described above, so that the slit 84 becomes situated at the location where it is suspected that certain microorganisms are present.

After the container 82 of FIG. 7 remains in the interior of the body for a given time, the conditions prevailing in the interior of the body cavity will cause the ring 94 to dissolve and thus release the container 82 so that by its own resiliency it will expand back to its initial condition shown in solid lines in FIG. 7. The result is that during this expansion fluids in the body cavity with suspected microorganisms in these fluids are drawn into the interior of the container 82 of FIG. 7 so as to engage the nutrient means 86 therein.

Of course, with the embodiment of FIG. 7 it is also possible initially to locate the device 82 in a cup-shaped body of soft material as described above. However, it is to be emphasized that with the embodiments of FIGS. 5–7 as well as with those of FIGS. 1–3 it is not absolutely essential to provide the cup-shaped body with soft material. The devices of the invention are relatively small and normally will not create any particular discomfort even if they are introduced without the use of a cup-shaped body as described above. The latter may be used, however, in those cases where it is felt that a particular individual may be particularly sensitive.

In all of the above-described embodiments there is situated within the container a nutrient medium which may be a suitable broth as referred to above. As a specific example, the nutrient medium may take the form of a Mueller Hinton Broth which may be present in an amount of, for example, 2.1 grams for each 100 ml total broth. With this latter broth there is contained in the total nutrient medium a certain amount of Agar which may be present in an amount of, for example 0.150 grams for each 100 ml of broth. Of course, in addition to the above ingredients the remainder of the broth will be made up of water. It is possible to increase the amount of Agar for each 100 ml of total nutrient medium up to 0.200 grams where the nutrient medium will start to congeal at 37° C. Thus, by varying the amount of Agar in the nutrient means it is possible to control the viscosity thereof.

In addition, as was pointed out above, the nutrient means will contain certain antibiotics for the purpose of preventing growth of microorganisms in which there is no interest and the growth of which may serve only to confuse the indication of the growth of a particular microorganism in which there is an interest. Such antibiotics may be the following which are present in the indicated amounts:

| Cholestimethate | 0.00563 | (5.6 mg) |
| Nystatin | 0.0090 | (9.0 mg) |
| Vancomycin | 0.0025 | (2.5 mg) |
| polymixin B | 0.00125 | (1.25 mg) |

Thus, antibiotics as set forth above may be included in the nutrient medium in the above amounts for each 100 ml of nutrient means.

The particular antibiotics referred to above will effectively kill E. coli, the growth of which might serve only to confuse the indication of the growth of other microoganisms.

Thus, it will be seen that with embodiments of the invention as shown in FIG. 1 and 10, the fact that the string or monofilament is frictionally pulled through the closure plugs will reliably prevent any reverse flow out of the container. In the same way, with the embodiments of FIG. 3, the building up of the pressure within the container after fluid is delivered into the latter by the wick or capillary tube will prevent the fluid delivered to the interior of the container from flowing back out of the container. Thus in the case of FIG. 3 the fluid cannot have access to the wick because of the pressure will build up in the interior of the container.

In the embodiment of FIG. 3 the outer tube 50 will prevent any liquid from having access to the wick.

Of course, all of the above-described embodiments which have flap valves will be reliably prevented by such flap valves from affording the possibility of flow out of the container. Those embodiments which have simply a small minute opening such as a pinhole 84, as shown in FIGS. 5 and 7, are also particularly effective in this respect. Thus, it is to be emphasized that these openings 84 are normally completely closed. They are formed, for example, by a small slit which passes through the wall of the container. As a result of the presence of such a small slit, which need not have a length greater than 1/32 of an inch, for example, during the expansion of the container the edges which form the slit will yield inwardly to permit inward flow of fluid. However, once the containers reach their initial configuration these slits 84 become completely closed to prevent any possibility of flow of fluid out of the containers 82. It is to be noted in this connection that the inward flow of fluid takes place in all embodiments of the invention over a relatively long period of time which is on the order of several hours, for example from six to twelve hours. This result is achieved also by way of the slit 84 which permits the fluid to flow into the interior of the container only at an extremely slow rate. Thus, with the embodiments of FIGS. 5 and 6, for example, when the containers 82 are deformed so as to push air out of the interiors of the containers, by the action of the bulges 90, these containers will not immediately resume their initial configuration. Because of the presence of the slit 84 it is not possible for air to be drawn rapidly back into the containers 82 and they remain in their compressed condition of restricted interior volume over a long period of time requiring several hours before the containers 82 resume their initial condition. The same effect of several hours of delivery of fluid at an extremely slow rate to the interior of the container is achieved with the other embodiments, with the possible exception of FIG. 1 the operator manipulates a string for this purpose. However it is to be emphasized that with these embodiments the operator will not manipulate the string to pull the suspected microorganism into the container until after the container has remained in the body cavity for a period of time sufficient to enable the entire device of the invention to assume, throughout all parts of the device of the invention, the temperature of the body in whose cavity the device is placed. Thus, it is known from experience that one of the most serious drawbacks of transferring microorganisms by way of a swab from the interior of a body to a suitable plate at the exterior of the body on which growth is to take place resides in the fact that the microorganisms are of necessity subjected to a change in temperature during such transfer operations. A temperature change which need only be on the order of 2° may be sufficient to kill certain microorganisms so that they will never grow and a test will be negative when in fact the microorganisms are present in the body. It is precisely such a drawback which is avoided with the present invention. Because the microorganism is drawn into the container of the invention over a long period of time, the device of the invention will be uniformly, throughout all of its parts, at the body temperature during travel of microorganism to the nutrient in the container of the invention. This factor, of course, shows the significance of the ring of FIG. 7. The ring 94 of FIG. 7 will only dissolve, as a result of the temperature of the body, after a given period of time whereby it is assured that the device of FIG. 7 will be at body temperature before any microorganisms reach the nutrient 86. However, the same advantages are achieved with the embodiment of FIG. 1, as pointed out above, simply by delaying the pulling of the string until after the device has remained in the body for a sufficient length of time to assure a uniform body temperature throughout the entire device of the invention. Of course, those embodiments which have wicks will assure accurate indications of the present or absence of certain microorganisms because they continue to deliver the fluid to the nutrient over a period of several hours.

The above-discussed important feature of the invention according to which a reverse flow of fluid out of the container back to the body is reliably avoided is carried out, in principle, even after the device is removed from the body. thus it is equally important to prevent contamination of individuals who handle the device of the invention. Therefore, where inspection alone of the nutrient through the clear transparent wall of the container of the invention will not give the required information, it is possible to use certain dyes in order to bring out the presence or absence of suspected microorganisms with great clarity. Such dyes are readily introduced into the interior of the container of the invention without opening the container, so that the operator need never touch the nutrient medium within the container. For example one or more drops of a suitable die can be introduced by way of a syringe the needle of which simply punctures through the wall of the container to enable the required amount of dye to be dropped onto the nutrient. In addition, where there are wicks, it is possible simply to apply the dye to a wick which will draw the dye into the container in order to spread the dye over the nutrient medium in order to give the required indication.

In connection with the nutrient means, as indicated above, it is not essential that this nutrient means be in the form of a liquid alone, since it can be absorbed in a suitable fibrous absorbent medium and can even be in a completely dry condition with the particular embodiment of the invention which is illustrated in FIG. 11 making special use of this latter type of nutrient.

Referring now to the embodiment of the invention which is illustrated in FIG. 8, it is desirable in connection with certain microorganisms to provide special atmospheres in which the microorganisms will have favorable growth conditions. For example certain microorganisms readily grow in a carbon dioxide atmosphere. With an arrangement as shown in FIG. 8 it is possible to provide such an atmosphere. The device 144 of FIG. 8 includes a container 146 which has its end walls traversed by a string 28, as shown in FIG. 8. However, the top end 148 of the container 146 is formed with an opening which is closed by a plug 150, and joined to the exterior surface of the top end 148 is a small flexible enclosure 152 made of a suitable plastic and containing a liquid 154, such as acetic acid. Situated directly on the nutrient 26 in the container 146 is a pellet 156 which may be a bicarbonate pellet. Just before the device of FIG. 8 is introduced into the body cavity, the flexible enclosure 152 is compressed so as to force the liquid 154 into the container 146 with the plug 150 yielding at this time as a result of the pressure applied to the container 152. When the acetic acid engages the pellet 156 there will be an automatic generation of carbon dioxide gas which fills the interior of the container 146 so as to provide an atmosphere which is highly favorable for the growth of certain microorganisms.

Although the devices of the invention may be made in various sizes and shapes, as a particular example, the total lengths of any of the above containers may be on the order of 1 inch while its diameter is on the order of 0.3 inches. The cup shaped body 34 will have a total length on the order of 1.5 inches and an outer diameter of approximately ½ inch, when used in the vagina.

What is claimed is:

1. For use in connection with the growing of cultures in the interior of a cavity of a body of a human being or animal, enclosure means having a size and configuration suitable for occupying a position in a body cavity with one part of said enclosure means situated adjacent a location where the presence of one or more predetermined microorganisms is suspected and with said enclosure means being closed at least to an extent sufficient to prevent escape of fluids from the interior to the exterior of said enclosure means, nutrient means for growing a culture from a given microorganism, said nutrient means being situated in said enclosure means at another part thereof, and transfer means situated at said one part of said enclosure means for transferring a microorganism from the exterior to the interior of said enclosure means into contact with the nutrient means while said enclosure means remains closed to said extent sufficient to prevent escape of fluids from the interior to the exterior of said enclosure means.

2. The combination of claim 1 and wherein said enclosure means carries at said one part thereof and at a part opposed to said one part thereof a pair of closure plug means which completely close said enclosure means, said transfer means including a string passing through said pair of closure plug means and frictionally engaged thereby so that said string can be drawn at least partially through said pair of closure plug means, said string carrying at an initial position of said string with respect to said pair of closure plug means a receiving means for receiving a microorganism, said receiving means being capable of being pulled with said string through said closure plug means at said one part of said enclosure means and into engagement with said nutrient means to transfer a microorganism into contact with said nutrient means.

3. The combination of claim 2 and wherein said string carries in the interior of said enclosure means between said pair of closure plug means an enlargement for limiting the extent of movement of said string with respect to said enclosure means.

4. The combination of claim 1 wherein said enclosure means is completely closed except at said one part thereof where said enclosure means is formed with an opening passing through a wall of said enclosure means, and said transfer means including a wick which completely fills and closes said opening while being capable of transferring a body fluid containing a microorganism through said opening into the interior of said enclosure means to form therein a drop capable of falling from said wick to said nutrient means.

5. The combination of claim 1 and wherein said enclosure means is made of clear transparent material through which the nutrient means can be inspected.

6. The combination of claim 1 and wherein said enclosure means is flexible and is initially in a compressed condition having a restricted interior volume, and holding means cooperating with said enclosure means for holding the latter in the compressed condition with said restricted interior volume until after the enclosure means is situated in the body cavity, said holding means being operable for then releasing said enclosure means for expansion in the body cavity and said enclosure means being formed at said part thereof with a minute opening forming said transfer means and through which a microorganism can transfer from the exterior to the interior of said enclosure means during expansion of said enclosure means.

7. The combination of claim 6 and wherein said holding means includes a tube through which said enclosure means passes while being introduced into the body cavity, said tube having an interior bulging portion which compresses said enclosure means and maintains the latter in said condition of restricted volume until after said enclosure means moves beyond said bulging portion of said tube into the body cavity.

8. The combination of claim 7 and wherein a flap valve is situated in the interior of said enclosure means at said one part thereof for closing said minute opening until said enclosure means expands after moving beyond said bulging portion of said tube, said flap valve permitting flow from the exterior to the interior of said enclosure means through said minute opening while preventing flow from the interior to the exterior of said enclosure means.

9. The combination of claim 6 and wherein said holding means includes a member of dissolvable material, capable of dissolving in response to conditions encountered in the body cavity while initially compressing said enclosure means to maintain the latter in the compressed condition of restricted interior volume, whereby after the enclosure means is situated in the body cavity, said member dissolves to release said enclosure means for expansion while a microorganism can pass through said minute opening into the interior of said enclosure means.

10. The combination of claim 1 and wherein a cup-shaped body of soft material carries said enclosure means with said one part thereof situated at an opening of said cup shaped-body, whereby the latter will prevent any discomfort upon situation of said enclosure means in the body cavity.

11. The combination of claim 10 and wherein an outer elongated tube initially carries said cup-shaped body in preparation for introduction of the latter together with said enclosure means into a body cavity, and a pusher slidable in said outer tube for engaging said cup-shaped body and displacing the latter out of said outer tube into the body cavity.

12. The combination of claim 1 and wherein said nutrient means is provided with antibiotics for preventing growth of at least some microorganisms which are different from a particular microorganism which is intended to grow in the nutrient means if said particular microorganism is present.

13. The combination of claim 1 and wherein said enclosure means has a pair of opposed wall portions which are closed and said transfer means including a string passing through said pair of opposed wall portions and frictionally engaged thereby so that said string can be drawn at least partially through said pair of opposed wall portions, said string carrying at an initial position of said string with respect to said pair of opposed wall portions a receiving means for receiving a microorganism, said receiving means being capable of being pulled with said string through one of said wall portions into engagement with said nutrient means to transfer a microorganism into contact with said nutrient means.

14. The combination of claim 1 and wherein said enclosure means carries a means for generating in the interior of said enclosure means a gas which favors the growth of said given microorganism.

* * * * *